(12) United States Patent
Pilla

(10) Patent No.: US 7,744,524 B2
(45) Date of Patent: Jun. 29, 2010

(54) APPARATUS AND METHOD FOR ELECTROMAGNETIC TREATMENT OF PLANT, ANIMAL, AND HUMAN TISSUE, ORGANS, CELLS, AND MOLECULES

(75) Inventor: Arthur A. Pilla, Oakland, NJ (US)

(73) Assignee: Ivivi Health Sciences, LLC, San Francisco, CA (US)

( * ) Notice: Subject to any disclaimer, the term of this patent is extended or adjusted under 35 U.S.C. 154(b) by 1459 days.

(21) Appl. No.: 11/003,108

(22) Filed: Dec. 3, 2004

(65) Prior Publication Data
US 2005/0197522 A1 Sep. 8, 2005

Related U.S. Application Data

(60) Provisional application No. 60/527,327, filed on Dec. 5, 2003.

(51) Int. Cl.
*A61N 1/00* (2006.01)
(52) U.S. Cl. ....................................................... 600/14
(58) Field of Classification Search ............... 600/9–15; 607/2, 3, 44–46, 50, 51, 59
See application file for complete search history.

(56) References Cited

U.S. PATENT DOCUMENTS

| | | | |
|---|---|---|---|
| 4,315,503 A | 2/1982 | Ryaby | |
| 5,000,178 A * | 3/1991 | Griffith | 607/2 |
| 5,181,902 A | 1/1993 | Erickson | |
| 5,224,922 A * | 7/1993 | Kurtz | 600/13 |
| 5,338,286 A | 8/1994 | Abbott | |
| 5,723,001 A | 3/1998 | Pilla | |
| 5,743,844 A | 4/1998 | Tepper | |
| 5,877,627 A | 3/1999 | Fischer et al. | |
| 2003/0125769 A1 | 7/2003 | Brighton | |

OTHER PUBLICATIONS

EMF signals and ion/ligand binding kinetics:prediction of bioeffective waveform parameters. Pilla et al, Bioelectrochemistry and Bioenergetics, 48 (1999) 27-34, 8 pages.*
Low-intensity electromagnetic and mechanical modulation of bone growth and repair: are they equivalent? Journal of Orthopedic Science, Pilla, Arthur. (2002) 7:420-428, 9 pages.*
Arthur A. Pilla, "Weak Time-varying and Static Magnetic Fields: From Mechanisms to Therapeutic Applications", in Biological Effects of Electromagnetic Fields, P. Stavroulakis, ed.Springer Verlag, 2003, pp. 34-75.

* cited by examiner

*Primary Examiner*—Samuel G Gilbert
(74) *Attorney, Agent, or Firm*—Shay Glenn LLP

(57) ABSTRACT

An apparatus and method for electromagnetic treatment of plants, animals, and humans comprising: configuring at least one waveform according to a mathematical model having at least one waveform parameter, said at least one waveform to be coupled to a target pathway structure; choosing a value of said at least one waveform parameter so that said at least waveform is configured to be detectable in said target pathway structure above background activity in said target pathway structure; generating an electromagnetic signal from said configured at least one waveform; and coupling said electromagnetic signal to said target pathway structure using a coupling device.

45 Claims, 8 Drawing Sheets

APPARATUS AND METHOD FOR ELECTROMAGNETIC TREATMENT OF PLANT, ANIMAL, AND HUMAN TISSUE, ORGANS, CELLS, AND MOLECULES

This application claims the benefit of U.S. Provisional Application 60/527,327 filed Dec. 5, 2003.

BACKGROUND OF THE INVENTION

1. Field of the Invention

This invention pertains generally to an apparatus and a method for in vitro and in vivo therapeutic and prophylactic treatment of plant, animal, and human tissue, organs, cells and molecules. In particular, an embodiment according to the present invention pertains to use of non-thermal time-varying magnetic fields configured for optimal coupling to target pathway structures such as molecules, cells, tissue, and organs, using power and amplitude comparison analysis to evaluate a signal to thermal noise ratio ("SNR") in the target pathway structure. Another embodiment according to the present invention pertains to application of bursts of arbitrary waveform electromagnetic signals to target pathway structures such as molecules, cells, tissues, and organs using ultra lightweight portable coupling devices such as inductors and electrodes, and driver circuitry that can be incorporated into a positioning device such as knee, elbow, lower back, shoulder, foot, and other anatomical wraps, as well as apparel such as garments, footwear, and fashion accessories.

Yet another embodiment according to the present invention pertains to application of steady state periodic signals of arbitrary waveform electromagnetic signals to target pathway structures such as molecules, cells, tissues, and organs. Examples of therapeutic and prophylactic applications of the present invention are musculoskeletal pain relief, edema reduction, increased local blood flow, microvascular blood perfusion, wound repair, bone repair, osteoporosis treatment and prevention, angiogenesis, neovascularization, enhanced immune response, tissue repair, enhanced transudation, and enhanced effectiveness of pharmacological agents. An embodiment according to the present invention can also be used in conjunction with other therapeutic and prophylactic procedures and modalities such as heat, cold, ultrasound, vacuum assisted wound closure, wound dressing, orthopedic fixation devices, and surgical interventions.

2. Discussion of Related Art

It is now well established that application of weak non-thermal electromagnetic fields ("EMF") can result in physiologically meaningful in vivo and in vitro bioeffects. Time-varying electromagnetic fields, comprising rectangular waveforms such as pulsing electromagnetic fields ("PEMF"), and sinusoidal waveforms such as pulsed radio frequency fields ("PRF") ranging from several Hertz to an about 15 to an about 40 MHz range, are clinically beneficial when used as an adjunctive therapy for a variety of musculoskeletal injuries and conditions.

Beginning in the 1960's, development of modern therapeutic and prophylactic devices was stimulated by clinical problems associated with non-union and delayed union bone fractures. Early work showed that an electrical pathway can be a means through which bone adaptively responds to mechanical input. Early therapeutic devices used implanted and semi-invasive electrodes delivering direct current ("DC") to a fracture site. Non-invasive technologies were subsequently developed using electrical and electromagnetic fields. These modalities were originally created to provide a non-invasive "no-touch" means of inducing an electrical/mechanical waveform at a cell/tissue level. Clinical applications of these technologies in orthopaedics have led to approved applications by regulatory bodies worldwide for treatment of fractures such as non-unions and fresh fractures, as well as spine fusion. Presently several EMF devices constitute the standard armamentarium of orthopaedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

Cellular studies have addressed effects of weak low frequency electromagnetic fields on both signal transduction pathways and growth factor synthesis. It can be shown that EMF stimulates secretion of growth factors after a short, trigger-like duration. Ion/ligand binding processes at a, cell membrane are generally considered an initial EMF target pathway structure. The clinical relevance to treatments for example of bone repair, is upregulation such as modulation, of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Stimulation of transforming growth factor beta ("TGF-β") messenger RNA ("mRNA") with PEMF in a bone induction model in a rat has been shown. Studies have also demonstrated upregulation of TGF-β mRNA by PEMF in human osteoblast-like cell line designated MG-63, wherein there were increases in TGF-β1, collagen, and osteocalcin synthesis. PEMF stimulated an increase in TGF-β1 in both hypertrophic and atrophic cells from human non-union tissue. Further studies demonstrated an increase in both TGF-β1 mRNA and protein in osteoblast cultures resulting from a direct effect of EMF on a calcium/calmodulin-dependent pathway. Cartilage cell studies have shown similar increases in TGF-β1 mRNA and protein synthesis from EMF, demonstrating a therapeutic application to joint repair. U.S. Pat. No. 4,315,503 (1982) to Ryaby and U.S. Pat. No. 5,723,001 (1998) to Pilla typify the research conducted in this field.

However, prior art in this field applies unnecessarily high amplitude and power to a target pathway structure, requires unnecessarily long treatment time, and is not portable.

Therefore, a need exists for an apparatus and a method that more effectively modulates biochemical processes that regulate tissue growth and repair, shortens treatment times, and incorporates miniaturized circuitry and light weight applicators thus allowing the apparatus to be portable and if desired disposable. A further need exists for an apparatus and method that more effectively modulates biochemical processes that regulate tissue growth and repair, shortens treatment times, and incorporates miniaturized circuitry and light weight applicators that can be constructed to be implantable.

SUMMARY OF THE INVENTION

An apparatus and a method for delivering electromagnetic signals to human, animal and plant target pathway structures such as molecules, cells, tissue and organs for therapeutic and prophylactic purposes. A preferred embodiment according to the present invention utilizes a Power Signal to Noise Ratio ("Power SNR") approach to configure bioeffective waveforms and incorporates miniaturized circuitry and lightweight flexible coils. This advantageously allows a device that utilizes a Power SNR approach, miniaturized circuitry, and lightweight flexible coils, to be completely portable and if desired to be constructed as disposable and if further desired to be constructed as implantable.

Specifically, broad spectral density bursts of electromagnetic waveforms, configured to achieve maximum signal power within a bandpass of a biological target, are selectively applied to target pathway structures such as living organs, tissues, cells and molecules. Waveforms are selected using a unique amplitude/power comparison with that of thermal noise in a target pathway structure. Signals comprise bursts of at least one of sinusoidal, rectangular, chaotic and random wave shapes, have frequency content in a range of about 0.01 Hz to about 100 MHz at about 1 to about 100,000 bursts per second, and have a burst repetition rate from about 0.01 to about 1000 bursts/second. Peak signal amplitude at a target pathway structure such as tissue, lies in a range of about 1 µV/cm to about 100 mV/cm. Each signal burst envelope may be a random function providing a means to accommodate different electromagnetic characteristics of healing tissue. A preferred embodiment according to the present comprises a 20 millisecond pulse burst comprising about 5 to about 20 microsecond symmetrical or asymmetrical pulses repeating at about 1 to about 100 kilohertz within the burst. The burst envelope is a modified 1/f function and is applied at random repetition rates. A resulting waveform can be delivered via inductive or capacitive coupling.

It is an object of the present invention to configure a power spectrum of a waveform by mathematical simulation by using signal to noise ratio ("SNR") analysis to configure an optimized, bioeffective waveform then coupling the configured waveform using a generating device such as ultra lightweight wire coils that are powered by a waveform configuration device such as miniaturized electronic circuitry.

It is another object of the present invention to evaluate Power SNR for any target pathway structure such as molecules, cells, tissues and organs of plants, animals and humans using any input waveform, even if the electrical equivalents are non-linear as in a Hodgkin-Huxley membrane model.

It is another object of the present invention to provide a method and apparatus for treating plants, animals and humans using electromagnetic fields selected by optimizing a power spectrum of a waveform to be applied to a chosen biochemical target pathway structure such as a molecule, cell, tissue and organ of a plant, animal, and human.

It is another object of the present invention to employ significantly lower peak amplitudes and shorter pulse duration. This can be accomplished by matching via Power SNR, a frequency range in a signal to frequency response and sensitivity of a target pathway structure such as a molecule, cell, tissue, and organ, of plants, animals and humans.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

Preferred embodiments of the present invention will be described below in more detail, with reference to the accompanying drawings.

DETAILED DESCRIPTION

Figure 1:
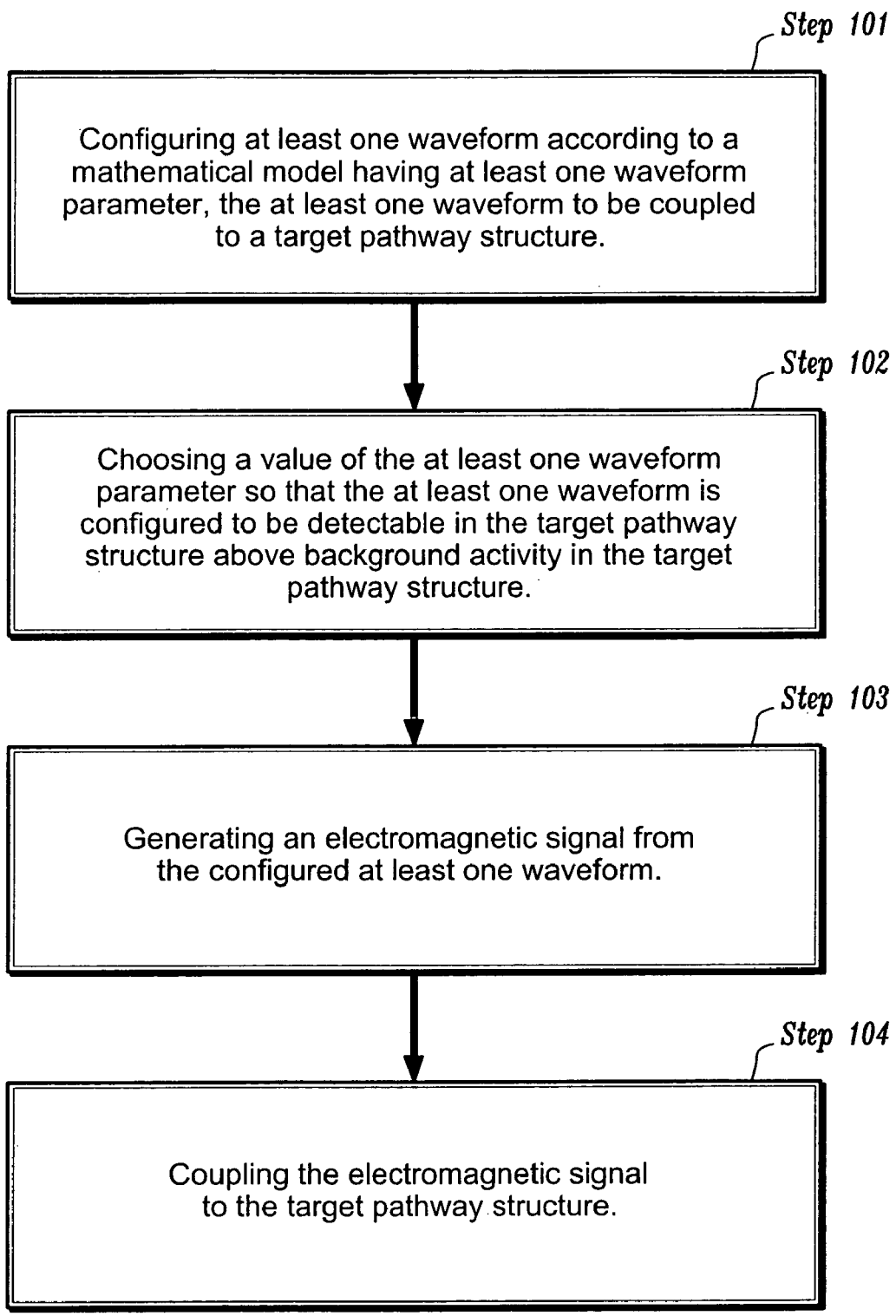
FIG. 1 is a flow diagram of a method for electromagnetic treatment of plant, animal, and human target pathway structures such as tissue, organs, cells, and molecules according to an embodiment of the present invention.

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of wound repair, for example bone repair, that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis is also integral to wound repair and modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ sec$^{-1}$, $[Ca^{2+}]=2.5$ μM, $K_D=30$ μM, $[Ca^{2+}CaM]=K_D$ $([Ca^{2+}]+[CaM])$, yields $k_b=665$ sec$^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4\ kT\ Re[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x,\omega)=\left[\frac{R_e+R_i+R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)=4\ kT\ Re[Z_M(x,\omega)]$ over all frequencies relevant to either complete membrane response, or to bandwidth of a target pathway structure. SNR can be expressed by a ratio:

$$SNR=\frac{|V_M(\omega)|}{RMS}$$

where $|V_M(\omega)|$ is maximum amplitude of voltage at each frequency as delivered by a chosen waveform to the target pathway structure.

Referring to FIG. 1, wherein FIG. 1 is a flow diagram of a method for delivering electromagnetic signals to target pathway structures such as molecules, cells, tissue and organs of plants, animals, and humans for therapeutic and prophylactic purposes according to an embodiment of the present invention. A mathematical model having at least one waveform parameter is applied to configure at least one waveform to be coupled to a target pathway structure such as a molecule, cell, tissue, and organ (Step 101). The configured waveform satisfies a SNR or Power SNR model so that for a given and known target pathway structure it is possible to choose at least one waveform parameter so that a waveform is detectable in the target pathway structure above its background activity (Step 102) such as baseline thermal fluctuations in voltage and electrical impedance at a target pathway structure that depend upon a state of a cell and tissue, that is whether the state is at least one of resting, growing, replacing, and responding to injury. A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 102). A repetitive electromagnetic signal can be generated for example inductively or capacitively, from said configured at least one waveform (Step 103). The electromagnetic signal is coupled to a target pathway structure such as a molecule, cell, tissue, and organ by output of a coupling device such as an electrode or an inductor, placed in close proximity to the target pathway structure (Step 104). The coupling enhances a stimulus to which cells and tissues react in a physiologically meaningful manner.

Figure 2:
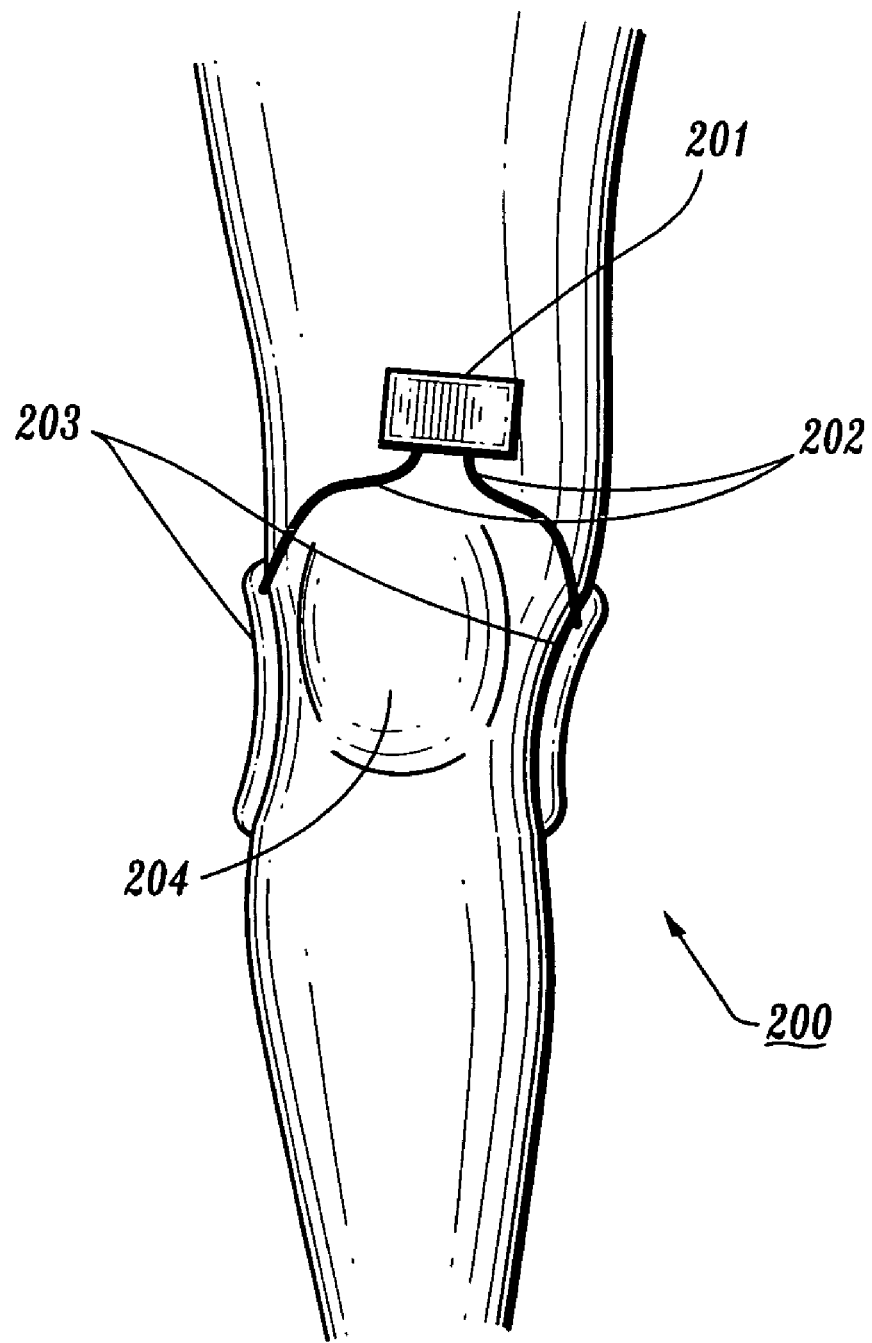
FIG. 2 is a view of control circuitry and electrical coils applied to a knee joint according to a preferred embodiment of the present invention.

FIG. 2 illustrates a preferred embodiment of an apparatus according to the present invention. A miniature control circuit 201 is coupled to an end of at least one connector 202 such as wire. The opposite end of the at least one connector is coupled to a generating device such as a pair of electrical coils 203. The miniature control circuit 201 is constructed in a manner that applies a mathematical model that is used to configure waveforms. The configured waveforms have to satisfy a SNR or Power SNR model so that for a given and known target pathway structure, it is possible to choose waveform parameters that satisfy SNR or Power SNR so that a waveform is detectable in the target pathway structure above its background activity. A preferred embodiment according to the present invention applies a mathematical model to induce a time-varying magnetic field and a time-varying electric field in a target pathway structure such as a molecule, cell, tissue, and organ, comprising about 10 to about 100 msec bursts of about 1 to about 100 microsecond rectangular pulses repeating at about 0.1 to about 10 pulses per second. Peak amplitude of the induced electric field is between about 1 uV/cm and about 100 mV/cm, varied according to a modified 1/f function where f=frequency. A Waveform configured using a preferred embodiment according to the present invention may be applied to a target pathway structure such as a molecule, cell, tissue, and organ for a preferred total exposure time of under 1 minute to 240 minutes daily. However other exposure times can be used. Waveforms configured by the miniature control circuit 201 are directed to a generating device 203 such as electrical coils via connector 202. The generating device 203 delivers a pulsing magnetic field configured according to a mathematical model, that can be used to provide treatment to a target pathway structure such as knee joint 204. The miniature control circuit applies a pulsing magnetic field for a prescribed time and can automatically repeat applying the pulsing magnetic field for as many applications as are needed in a given time period, for example 10 times a day. A preferred embodiment according to the present invention can be positioned to treat the knee joint 204 by a positioning device. The positioning device can be portable such as an anatomical support, and is further described below with reference to FIG. 6. Coupling a pulsing magnetic field to a target pathway structure such as a molecule, cell, tissue, and organ, therapeutically and prophylactically reduces inflammation thereby reducing pain and promotes healing. When electrical coils are used as the generating device 203, the electrical coils can be powered with a time varying magnetic field that induces a time varying electric field in a target pathway structure according to Faraday's law. An electromagnetic signal generated by the generating device 203 can also be applied using electrochemical coupling, wherein electrodes are in direct contact with skin or another outer electrically conductive boundary of a target pathway structure. Yet in another embodiment according to the present invention, the electromagnetic signal generated by the generating device 203 can also be applied using electrostatic coupling wherein an air gap exists between a generating device 203 such as an electrode and a target pathway structure such as a molecule, cell, tissue, and organ. An advantage of the preferred embodiment according to the present invention is that its ultra lightweight coils and miniaturized circuitry allow for use with common physical therapy treatment modalities and at any body location for which pain relief and healing is desired. An advantageous result of application of the preferred embodiment according to the present invention is that a living organism's wellbeing can be maintained and enhanced.

Figure 3:
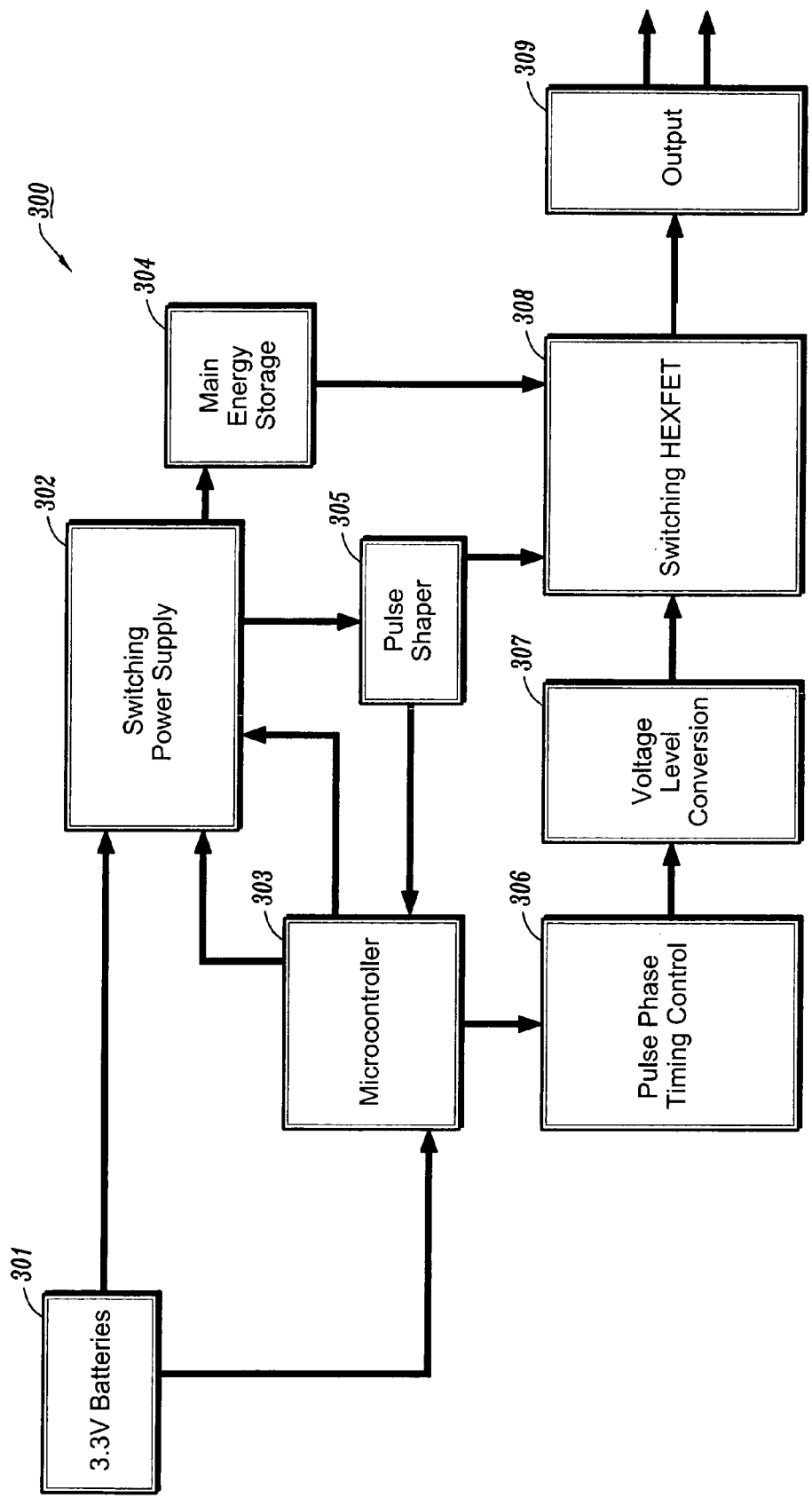
FIG. 3 is a block diagram of miniaturized circuitry according to a preferred embodiment of the present invention.

FIG. 3 depicts a block diagram of a preferred embodiment according to the present invention of a miniature control circuit 300. The miniature control circuit 300 produces waveforms that drive a generating device such as wire coils described above in FIG. 2. The miniature control circuit can be activated by any activation means such as an on/off switch. The miniature control circuit 300 has a power source such as a lithium battery 301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 302 controls voltage to a micro-controller 303. A preferred embodiment of the micro-controller 303 uses an 8 bit 4 MHz micro-controller 303 but other bit MHz combination micro-controllers may be used. The switching power supply 302 also delivers current to storage capacitors 304. A preferred embodiment of the present invention uses storage capacitors having a 220 uF output but other outputs can be used. The storage capacitors 304 allow high frequency pulses to be delivered to a coupling device such as inductors (Not Shown). The micro-controller 303 also controls a pulse shaper 305 and a pulse phase timing control 306. The pulse shaper 305 and pulse phase timing control 306 determine pulse shape, burst width, burst envelope shape, and burst repetition rate. An integral waveform generator, such as a sine wave or arbitrary number generator can also be incorporated to provide specific waveforms. A voltage level conversion sub-circuit 308 controls an induced field delivered to a target pathway structure. A switching Hexfet 308 allows pulses of randomized amplitude to be delivered to output 309 that routes a waveform to at least one coupling device such as an inductor. The micro-controller 303 can also control total exposure time of a single treatment of a target pathway structure such as a molecule, cell, tissue, and organ. The miniature control circuit 300 can be constructed to apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Figure 4A:
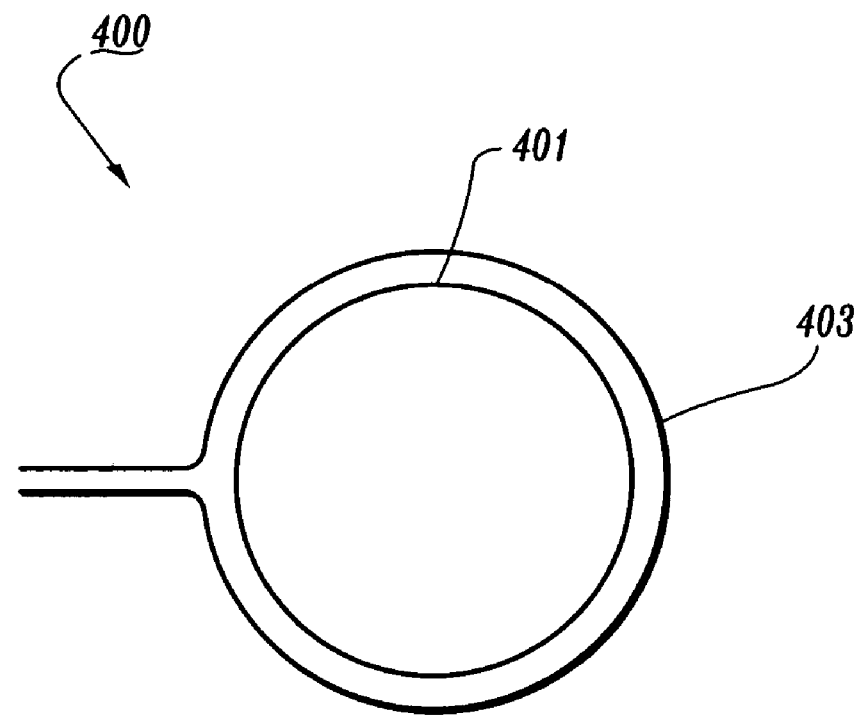
FIG. 4A is a line drawing of a wire coil such as an inductor according to a preferred embodiment of the present invention.
Figure 4B:
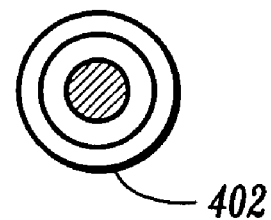
FIG. 4B is a line drawing of a flexible magnetic wire according to a preferred embodiment of the present invention.

Referring to FIGS. 4A and 4B a preferred embodiment according to the present invention of a coupling device 400 such as an inductor is shown. The coupling device 400 can be an electric coil 401 wound with multistrand flexible magnetic wire 402. The multistrand flexible magnetic wire 402 enables the electric coil 401 to conform to specific anatomical configurations such as a limb or joint of a human or animal. A preferred embodiment of the electric coil 401 comprises about 10 to about 50 turns of about 0.01 mm to about 0.1 mm diameter multistrand magnet wire wound on an initially circular form having an outer diameter between about 2.5 cm and about 50 cm but other numbers of turns and wire diameters can be used. A preferred embodiment of the electric coil 401 can be encased with a non-toxic PVC mould 403 but other non-toxic moulds can also be used.

Figure 5:
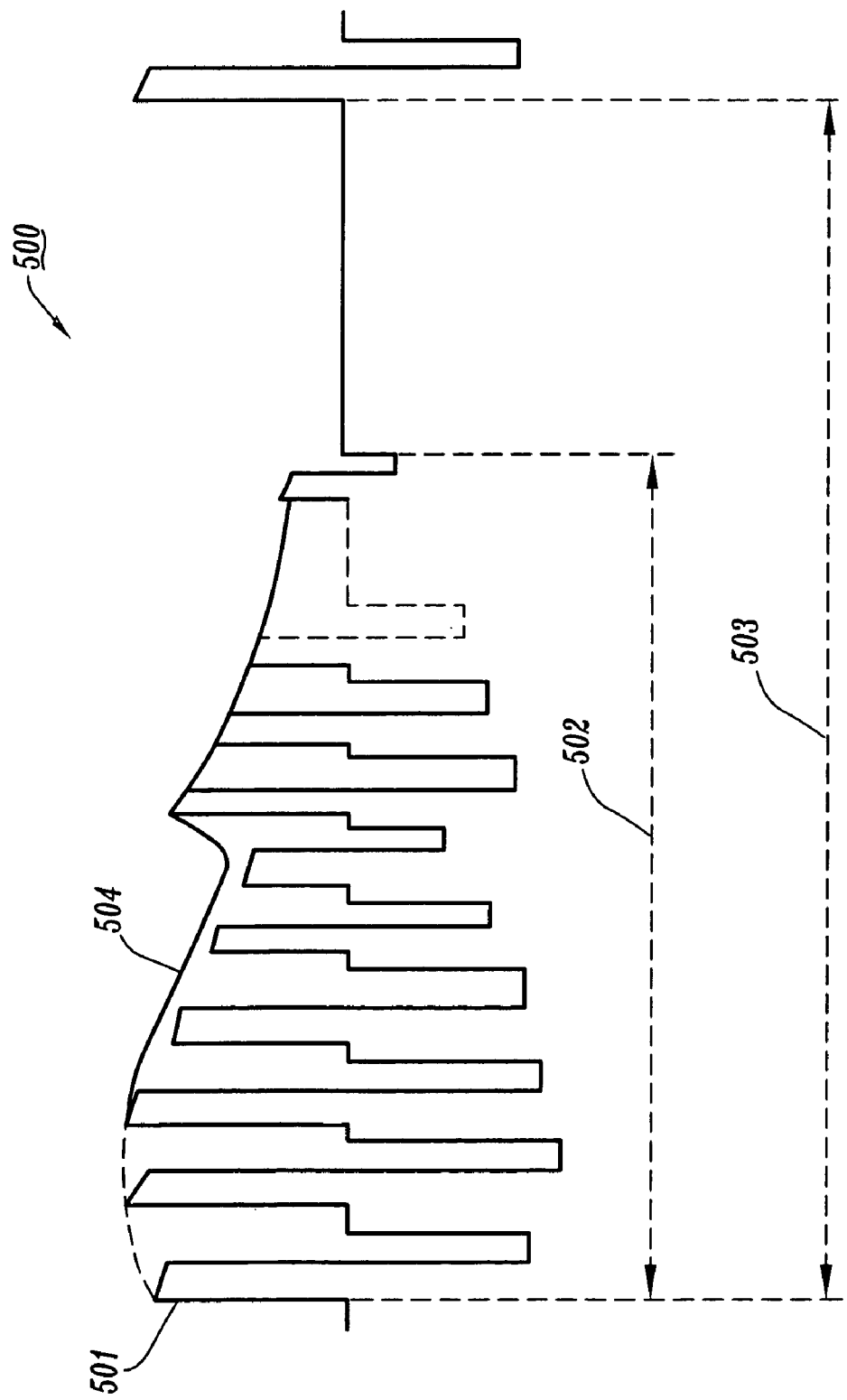
FIG. 5 depicts a waveform delivered to a target pathway structure such as a molecule, cell, tissue or organ according to a preferred embodiment of the present invention.

Referring to FIG. 5 an embodiment according to the present invention of a waveform 500 is illustrated. A pulse 501 is repeated within a burst 502 that has a finite duration 503. The duration 503 is such that a duty cycle which can be defined as a ratio of burst duration to signal period is between about 1 to about $10^{-5}$. A preferred embodiment according to the present invention utilizes pseudo rectangular 10 microsecond pulses for pulse 501 applied in a burst 502 for about 10 to about 50 msec having a modified 1/f amplitude envelope 504 and with a finite duration 503 corresponding to a burst period of between about 0.1 and about 10 seconds.

Figure 6:
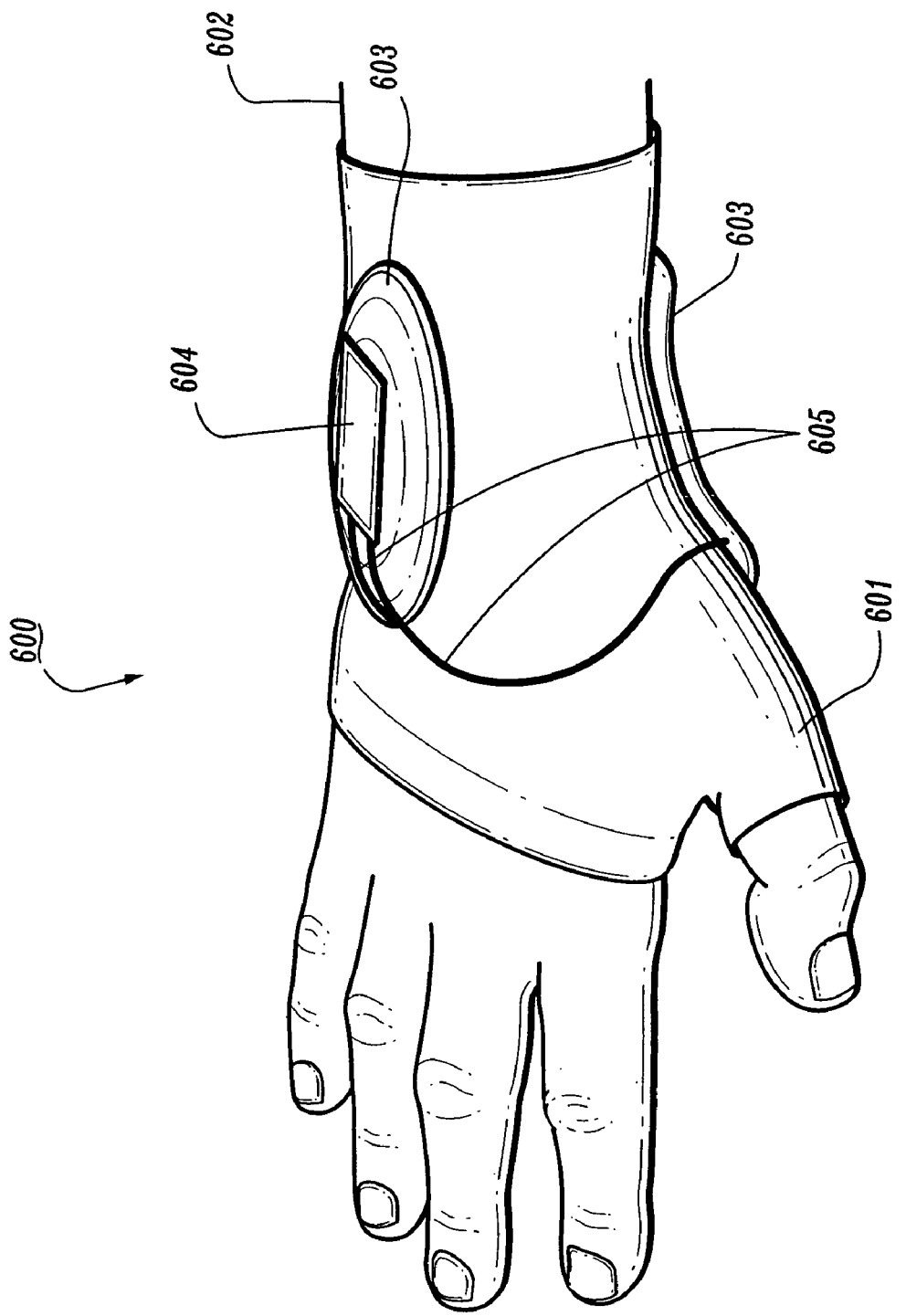
FIG. 6 is a view of a positioning device such as a wrist support according to a preferred embodiment of the present invention.

FIG. 6 illustrates a preferred embodiment according to the present invention of a positioning device such as a wrist support. A positioning device 600 such as a wrist support 601 is worn on a human wrist 602. The positioning device can be constructed to be portable, can be constructed to be disposable, and can be constructed to be implantable. The positioning device can be used in combination with the present invention in a plurality of ways, for example incorporating the present invention into the positioning device for example by stitching, affixing the present invention onto the positioning device for example by Velcro®, and holding the present invention in place by constructing the positioning device to be elastic. In another embodiment according to the present invention, the present invention can be constructed as a stand-alone device of any size with or without a positioning device, to be used anywhere for example at home, at a clinic, at a treatment center, and outdoors. The wrist support 601 can be made with any anatomical and support material, such as neoprene. Coils 603 are integrated into the wrist support 601 such that a signal configured according to the present invention, for example the waveform depicted in FIG. 5, is applied from a dorsal portion that is the top of the wrist to a plantar portion that is the bottom of the wrist. Micro-circuitry 604 is attached to the exterior of the wrist support 601 using a fastening device such as Velcro® (Not Shown). The micro-circuitry is coupled to one end of at least one connecting device such as a flexible wire 605. The other end of the at least one connecting device is coupled to the coils 603. Other embodiments according to the present invention of the positioning device include knee, elbow, lower back, shoulder, other anatomical wraps, and apparel such as garments, fashion accessories, and footwear.

Example 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCR") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA12. Free $Ca^{2+}$ was varied in the 1-7 µM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 µL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 µM 32 P ATP, and was stopped with Laemmli Sample Buffer solution containing 30 µM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32 P incorporated in MLC using a TM Analytic model 5303 Mark V liquid scintillation counter.

Figure 7:
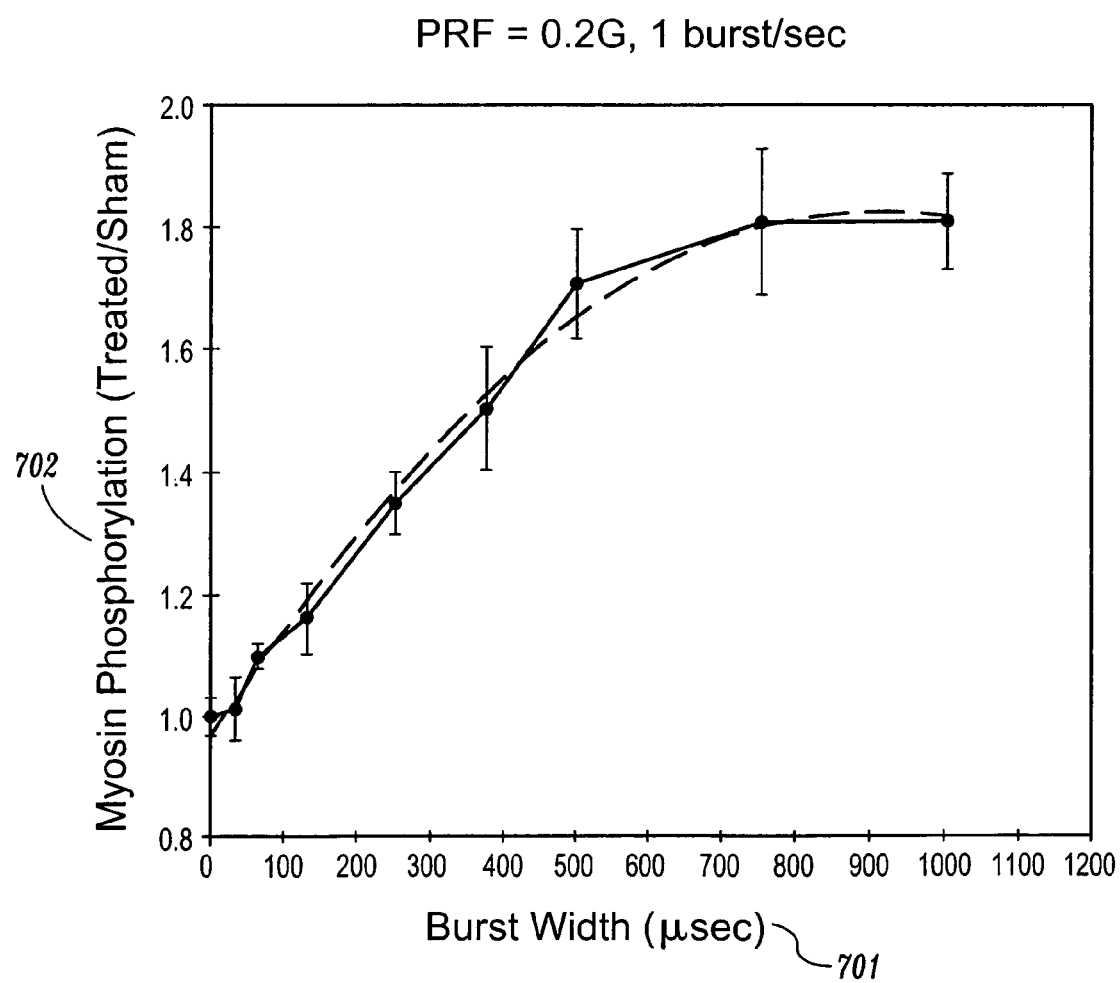
FIG. 7 is a graph illustrating maximally increased myosin phosphorylation for a PMRF signal configured according to an embodiment of the present invention.

The signal comprised repetitive bursts of a high frequency waveform. Amplitude was maintained constant at 0.2 G and repetition rate was 1 burst/sec for all exposures. Burst duration varied from 65 µsec to 1000 µsec based upon projections of Power SNR analysis which showed that optimal Power SNR would be achieved as burst duration approached 500 µsec. The results are shown in FIG. 7 wherein burst width 701 in µsec is plotted on the x-axis and Myosin Phosphorylation 702 as treated/sham is plotted on the y-axis. It can be seen that the PMF effect on $Ca^{2+}$ binding to CaM approaches its maximum at approximately 500 µsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

Example 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 µsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 µsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in kg/mm². The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per mm² of the two strips from the same wound.

The results showed average tensile strength for the 65 µsec 1 Gauss PRF signal was 19.3±4.3 kg/mm² for the exposed group versus 13.0±3.5 kg/mm² for the control group ($p<0.01$), which is a 48% increase. In contrast, the average tensile strength for the 2000 µsec 0.2 Gauss PRF signal, configured according to an embodiment of the present invention using a Power SNR model was 21.2±5.6 kg/mm² for the treated group versus 13.7±4.1 kg/mm² ($p<0.01$) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

Example 3

In this example Jurkat cells react to PMF stimulation of a T-cell receptor with cell cycle arrest and thus behave like normal T-lymphocytes stimulated by antigens at the T-cell receptor such as anti-CD3. For example in bone healing, results have shown both 60 Hz and PEMF fields decrease DNA synthesis of Jurkat cells, as is expected since PMF interacts with the T-cell receptor in the absence of a costimulatory signal. This is consistent with an anti-inflammatory response, as has been observed in clinical applications of PMF stimuli. The PEMF signal is more effective. A dosimetry analysis performed according to an embodiment of the present invention demonstrates why both signals are effective and why PEMF signals have a greater effect than 60 Hz signals on Jurkat cells in the most EMF-sensitive growth stage.

Comparison of dosimetry from the two signals employed involves evaluation of the ratio of the Power spectrum of the thermal noise voltage that is Power SNR, to that of the induced voltage at the EMF-sensitive target pathway structure. The target pathway structure used is ion binding at receptor sites on Jurkat cells suspended in 2 mm of culture medium. The average peak electric field at the binding site from a PEMF signal comprising 5 msec burst of 200 µsec pulses repeating at 15/sec, was 1 mV/cm, while for a 60 Hz signal it was 50 µV/cm.

Figure 8:
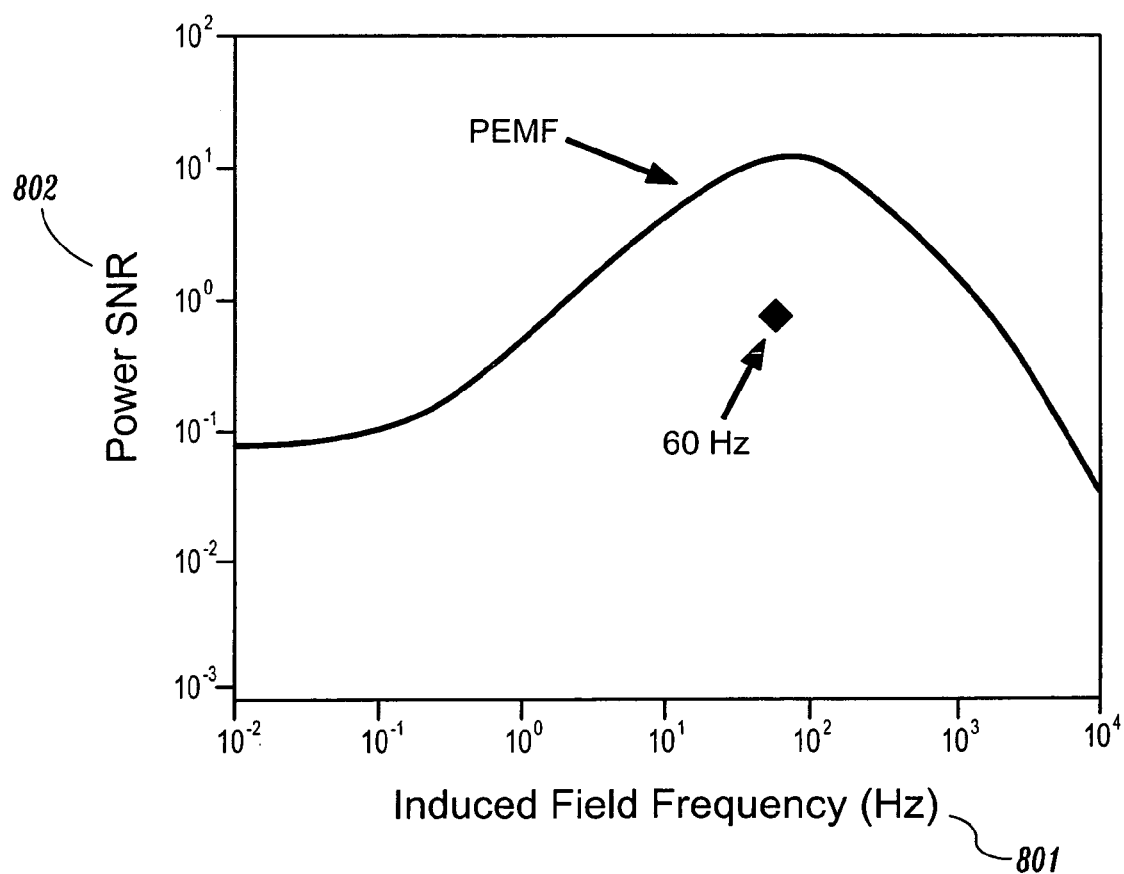
FIG. 8 is a graph illustrating a power consumption comparison between a 60 Hz signal and a PEMF signal configured according to an embodiment of the present invention.

FIG. 8 is a graph of results wherein Induced Field Frequency 801 in Hz is plotted on the x-axis and Power SNR 802 is plotted on the y-axis. FIG. 8 illustrates that both signals have sufficient Power spectrum that is Power SNR≈1, to be detected within a frequency range of binding kinetics. However, maximum Power SNR for the PEMF signal is significantly higher than that for the 60 Hz signal. This is because a PEMF signal has many frequency components falling within the bandpass of the binding pathway. The single frequency component of a 60 Hz signal lies at the mid-point of the bandpass of the target pathway. The Power SNR calculation that was used in this example is dependant upon $\tau_{ion}$ which is obtained from the rate constant for ion binding. Had this calculation been performed a priori it would have concluded that both signals satisfied basic detectability requirements and could modulate an EMF-sensitive ion binding pathway at the start of a regulatory cascade for DNA synthesis in these cells. The previous examples illustrated that utilizing the rate constant for Ca/CaM binding could lead to successful projections for bioeffective EMF signals in a variety of systems.

Having described embodiments for an apparatus and a method for delivering electromagnetic treatment to human, animal and plant molecules, cells, tissue and organs, it is noted that modifications and variations can be made by persons skilled in the art in light of the above teachings. It is therefore to be understood that changes may be made in the particular embodiments of the invention disclosed which are within the scope and spirit of the invention as defined by the appended claims.

What is claimed is:

1. An electromagnetic treatment apparatus for plants, animals, and humans comprising:

A waveform configuration means for configuring at least one waveform to be coupled to a target pathway structure according to a mathematical model having at least one waveform parameter capable of being chosen so that said at least one waveform is configured to be detectable in said target structure above background activity in said target pathway structure;

An electromagnetic signal generating means connected to said waveform device by at least one connecting means for generating an electromagnetic signal from said configured at least one waveform; and A coupling device connected by at least one connecting means to said electromagnetic signal generating device for coupling said electromagnetic signal to said target pathway structure.

2. The electromagnetic treatment apparatus of claim 1, wherein said target pathway structure includes at least one of a molecule, a cell, a tissue, and an organ.

3. The electromagnetic treatment apparatus of claim 1, wherein said at least one waveform parameter includes at least one of a frequency component parameter that configures said at least one waveform to be between about 0.01 Hz and about 100 MHz, a burst amplitude envelope parameter that follows an arbitrary amplitude function, a burst amplitude envelope parameter that follows a defined amplitude function, a burst width parameter that varies at each repetition according to an arbitrary width function, a burst width parameter that varies at each repetition according to a defined width function, a peak induced electric field parameter varying between about 1 µV/cm and about 100 mV/cm in said target pathway structure, and a peak induced magnetic electric field parameter varying between about 1 µT and about 0.1 T in said target pathway structure.

4. The electromagnetic treatment apparatus of claim 1, wherein said defined amplitude function includes at least one of a 1/frequency function, a logarithmic function, a chaotic function and an exponential function.

5. The electromagnetic treatment apparatus of claim 1, wherein a value of said at least one waveform parameter is chosen to satisfy a Signal to Noise Ratio model.

6. The electromagnetic treatment apparatus of claim 1, wherein a value of at least one waveform parameter is chosen to satisfy a Power Signal to Noise Ratio model.

7. The electromagnetic treatment apparatus of claim 1, wherein said electromagnetic signal generating device includes an inductive generating device.

8. The electromagnetic treatment apparatus of claim 1, wherein said electromagnetic signal generating device includes a capacitive generating device.

9. The electromagnetic treatment apparatus of claim 1, wherein said coupling device includes an inductor.

10. The electromagnetic treatment apparatus of claim 1, wherein said coupling device includes an electrode.

11. The electromagnetic treatment apparatus of claim 1, further comprising a positioning device to position said electromagnetic treatment apparatus for delivering treatment to said plants, animals and humans.

12. The electromagnetic treatment apparatus of claim 11, wherein said positioning device is at least one of an anatomical support, an anatomical wrap, and apparel.

13. The electromagnetic treatment apparatus of claim 12, wherein said apparel includes at least one of garments, fashion accessories, and footwear.

14. The electromagnetic treatment apparatus of claim 11, wherein said positioning device is portable.

15. The electromagnetic treatment apparatus of claim 11, wherein said positioning device is disposable.

16. The electromagnetic treatment apparatus of claim 11, wherein said positioning device is implantable.

17. A method for electromagnetic treatment of plants, animals, and humans comprising the steps of:
  Configuring at least one waveform using the apparatus of claim 1 according to a mathematical model having at least one waveform parameter, said at least one waveform to be coupled to a target pathway structure;
  Choosing a value of said at least one waveform parameter so that said at least waveform is configured to be detectable in said target pathway structure above background activity in said target pathway structure;
  Generating an electromagnetic signal from said configured at least one waveform; and
  Coupling said electromagnetic signal to said target pathway structure using a coupling device.

18. The method of claim 17, wherein said target pathway structure includes at least one of a molecule, a cell, a tissue, and an organ.

19. The method of claim 17, wherein said at least one waveform parameter includes at least one of a frequency component parameter that configures said at least one waveform to be between about 0.01 Hz and about 100 MHz, a burst amplitude envelope parameter that follows an arbitrary amplitude function, a burst amplitude envelope parameter that follows a defined amplitude function, a burst width parameter that varies at each repetition according to an arbitrary width function, a burst width parameter that varies at each repetition according to a defined width function, a peak induced electric field parameter varying between about 1 µV/cm and: about 100 mV/cm in said target pathway structure, and a peak induced magnetic electric field parameter varying between about 1 µT and about 0.1 T in said target pathway structure.

20. The method of claim 19, wherein said defined amplitude function includes at least one of a 1/frequency function, a logarithmic function, a chaotic function, and an exponential function.

21. The method of claim 17, wherein said step of choosing a value of at least one waveform parameter further includes the step of choosing a value of said at least one waveform parameter to satisfy a Signal to Noise Ratio model.

22. The method of claim 17, wherein said step of choosing a value of at least one waveform parameter further includes the step of choosing a value of said at least one waveform parameter to satisfy a Power Signal to Noise Ratio model.

23. The method of claim 17 wherein said step of generating an electromagnetic signal further includes the step of inductive generation of said electromagnetic signal.

24. The method of claim 17, wherein said step of generating an electromagnetic signal further includes the step of capacitive generation of said electromagnetic signal.

25. The method of claim 17, wherein said step of coupling said electromagnetic signal further includes the step of coupling said electromagnetic signal electrochemically to said target pathway structure.

26. The method of claim 17, wherein said step of coupling said electromagnetic signal further includes the step of coupling said electromagnetic signal electrostatically to said target pathway structure.

27. The method of claim 17, wherein said coupling device includes an inductor.

28. The method of claim 17, wherein said coupling device includes an electrode.

29. The method of claim 17, further comprising the step of using at least one of standard medical therapies and non-standard medical therapies adjunctively with said electromagnetic treatment.

30. The method of claim 17, further comprising the step of using at least one of standard physical therapies and non-standard physical therapies conjunctively with said electromagnetic treatment.

31. The method of claim 17, further comprising the step of using said electromagnetic treatment to modulate the production and utilization of growth factors, cytokines, and regulatory substances by living cells.

32. The method of claim 17, further comprising the step of using said electromagnetic treatment to modulate tissue growth and repair.

33. The method of claim 17, further comprising the step of using said electromagnetic treatment to reduce chronic and acute pain of musculoskeletal and neural origin.

34. The method of claim 17, further comprising the step of using said electromagnetic treatment to reduce edema.

35. The method of claim 17, further comprising the step of using said electromagnetic treatment for treatment of diabetic and pressure ulcers wherein said ulcers are chronic.

36. The method of claim 17, further comprising the step of using said electromagnetic treatment for at least one of increasing blood flow and microvascular blood perfusion.

37. The method of claim 17, further comprising the step of using said electromagnetic treatment for at least one of neovascularization and angiogenesis.

38. The method of claim 17, further comprising the step of using said electromagnetic treatment to enhance immune response for malignant and benign conditions.

39. The method of claim 17, further comprising the step of using said electromagnetic treatment to enhance transudation.

40. The method of claim 17, further comprising the step of using a positioning device to deliver said electromagnetic treatment to said plants, animals, and humans.

41. The method of claim 40, wherein said positioning device comprises at least one of an anatomical support, an anatomical wrap, and apparel.

42. The method of claim 40, wherein said apparel includes at least one of garments, fashion accessories, and footwear.

43. The method of claim 40, wherein said positioning Device is portable.

44. The method of claim 40, wherein said positioning device is disposable.

45. The method of claim 40, wherein said positioning Device is implantable.

* * * * *